(12) United States Patent
Herndon et al.

(10) Patent No.: US 9,345,487 B2
(45) Date of Patent: May 24, 2016

(54) PRECISION BONE DRILL AND METHOD OF USE

(71) Applicant: Path Scientific, LLC, Carlisle, MA (US)

(72) Inventors: Terry Herndon, Carlisle, MA (US); Thiruvallur R. Gowrishankar, Acton, MA (US)

(73) Assignee: Path Scientific, LLC, Carlisle, MA (US)

( * ) Notice: Subject to any disclaimer, the term of this patent is extended or adjusted under 35 U.S.C. 154(b) by 2 days.

(21) Appl. No.: 14/171,860

(22) Filed: Feb. 4, 2014

(65) Prior Publication Data

US 2014/0222003 A1 Aug. 7, 2014

Related U.S. Application Data

(63) Continuation-in-part of application No. 14/096,075, filed on Dec. 4, 2013, now Pat. No. 9,022,949.

(60) Provisional application No. 61/760,856, filed on Feb. 5, 2013.

(51) Int. Cl.
*A61B 17/00* (2006.01)
*A61B 17/16* (2006.01)
*A61B 5/053* (2006.01)
(Continued)

(52) U.S. Cl.
CPC ............... *A61B 17/16* (2013.01); *A61B 5/053* (2013.01); *A61B 17/1622* (2013.01); *A61B 17/1626* (2013.01); *A61B 17/205* (2013.01); *A61B 2017/00026* (2013.01); *A61B 2017/00747* (2013.01); *A61B 2018/00875* (2013.01)

(58) Field of Classification Search
CPC ............................ A61B 17/1695; A61B 17/16
USPC ............. 600/547; 606/80; 125/1; 29/407.05, 29/593, 1 R, 12, 15, 7; 408/146, 103, 108, 408/109, 136, 180; 175/20, 50, 55, 58, 87, 175/122, 170, 203, 316
See application file for complete search history.

(56) References Cited

U.S. PATENT DOCUMENTS 3,785,230 A 1/1974 Lokey
3,918,449 A 11/1975 Pistor
4,391,358 A 7/1983 Haeger
(Continued)

OTHER PUBLICATIONS

USPTO Non-Final Office Action for U.S. Appl. No. 14/096,075 dated Oct. 2, 2014.
(Continued)

*Primary Examiner* — Brian Szmal

(57) ABSTRACT

Disclosed is a drilling device and a method for the drilling of human or animal bone tissue. The method comprises the following steps; (a) providing a drill having an electrically conductive bone cutter and an electrically conducting nosepiece assembly spaced apart from the electrically conductive bone cutter and acting as a counter electrode; (b) placing the electrically conductive bone cutter and nosepiece assembly into contact with the bone tissue to be drilled; (c) measuring the electrical impedance between the bone cutter tip and the nosepiece or the current through the cutter motor; (d) commencing drilling and moving the bone cutter toward the bone surface; (e) starting a step counter when the impedance reduces or the cutter motor current increases; (f) incrementing the step counter with every step of the vertical drive motor until the step count reaches the prespecified value thereby controlling the depth of the hole drilled.

21 Claims, 6 Drawing Sheets

| 1 – Plastic Housing | 2 – Motor Coupling | 3 – Vertical Drive Motor (Stepper Motor) |
|---|---|---|
| 4 – Printed Circuit Board | 5 – Top Plate | 6 – Cutter Motor |
| 7 – Actuator Switch | 8 – Nosepiece | 9 – Bone Cutter |
| 10 – Stationary Frame | 11 – Moving Carriage | 12 – Guide Pins |
| 13 – Nut Keeper | 14 – LED | 15 – Bottom Plate |
| 16 – Lead Nut | 17 – Lead Screw | 18 – Chuck |
| 19 – Cutter Motor Plate | 20 – PCB Spacer | 21 – Vertical Drive Motor Plate |
| 22 – Lock Nut | | |

(51) Int. Cl.
*A61B 17/20* (2006.01)
*A61B 18/00* (2006.01)

(56) References Cited

U.S. PATENT DOCUMENTS

| | | |
|---|---|---|
| 5,115,567 A | 5/1992 | Yang et al. |
| 5,135,532 A | 8/1992 | Baker |
| 5,272,948 A | 12/1993 | Theising |
| 5,283,955 A | 2/1994 | Liang |
| 5,611,808 A | 3/1997 | Hossain et al. |
| 5,630,796 A | 5/1997 | Bellhouse et al. |
| 5,645,554 A | 7/1997 | Hugh |
| 5,843,114 A | 12/1998 | Jang |
| 6,136,008 A | 10/2000 | Becker et al. |
| 6,176,865 B1 | 1/2001 | Mauze et al. |
| 6,207,400 B1 | 3/2001 | Kwon |
| 6,301,500 B1 | 10/2001 | Van Herk et al. |
| 6,334,856 B1 | 1/2002 | Allen et al. |
| 6,391,005 B1 | 5/2002 | Lum et al. |
| 6,402,732 B1 | 6/2002 | Flower et al. |
| 6,569,143 B2 | 5/2003 | Alchas et al. |
| 6,572,580 B2 | 6/2003 | Feldman |
| 6,706,032 B2 | 3/2004 | Weaver et al. |
| 7,205,738 B2 | 4/2007 | Chapman et al. |
| 2004/0204700 A1 | 10/2004 | Weaver et al. |
| 2004/0236269 A1 | 11/2004 | Marchitto et al. |
| 2005/0119660 A1 | 6/2005 | Bourlion et al. |
| 2006/0247795 A1 | 11/2006 | Gass et al. |

OTHER PUBLICATIONS

Zipp, Medical & Biological Engineering & Computing, May 1983 pp. 382-384.

PATHFORMER DEVICE-2

Parts:

1. Shell
2. Movable Carriage
3. Stationary Frame
4. Cutter
5. Illumination LED
6. Circuit Board
7. Foot
8. Guide Pins
9. Top Plate
10. Lead Screw Nut
11. Lead Screw
12. Bottom Plate
13. Drive Switch

| 1 – Plastic Housing | 2 – Motor Coupling | 3 – Vertical Drive Motor (Stepper Motor) |
| --- | --- | --- |
| 4 – Printed Circuit Board | 5 – Top Plate | 6 – Cutter Motor |
| 7 – Actuator Switch | 8 – Nosepiece | 9 – Bone Cutter |
| 10 – Stationary Frame | 11 – Moving Carriage | 12 – Guide Pins |
| 13 – Nut Keeper | 14 – LED | 15 – Bottom Plate |
| 16 – Lead Nut | 17 – Lead Screw | 18 – Chuck |
| 19 – Cutter Motor Plate | 20 – PCB Spacer | 21 – Vertical Drive Motor Plate |
| 22 – Lock Nut | | |

PRECISION BONE DRILL AND METHOD OF USE

CROSS-REFERENCE TO RELATED APPLICATIONS

This application is a continuation-in-part of commonly owned copending U.S. patent application Ser. No. 14/096,075, filed Dec. 4, 2013, the disclosure of which is hereby incorporated herein by reference. This application also claims benefit of U.S. Provisional Patent Application Ser. No. 61/760,856 filed Feb. 5, 2013, the disclosure of which is hereby incorporated herein by reference.

FIELD OF THE INVENTION

This invention is directed to a drilling device and a drilling procedure for drilling holes in live human or animal bones. The device is equipped with a rotating drilling drive that includes an automatic stop and withdraw mechanism to ensure precision of depth of drilling.

BACKGROUND OF THE INVENTION

Orthopedic and neurological surgeries involve drilling bone to accurate depths. For example, it is often desired that the drill bit does not contact and/or damage the soft tissues and nerves beyond the far cortex of the bone. See, for example U.S. Pat. No. 5,601,557, the disclosure of which is hereby incorporated herein by reference. The '557 patent discloses drilling a hole through the hard outer shell of bone into the less dense cancellous bone followed by a surgeon inserting a small, but resilient device (an "anchor") by pressing it into the smaller drilled hole. The anchor compresses as it passes through that hole, but once in the softer cancellous bone, the resilience causes it to expand again, causing it to stay in place. The attached anchor is then used to secure tissues to the bone, e.g., for repair of damaged ligaments and the like.

Orthopedic surgery and trauma care often require bone drilling when repair of fractures is indicated. The holes resulting from such drilling can accept screws to hold implants such as plates, prostheses or to exert pressure between broken and subsequently reduced bone fragments. The screws inserted have to fit properly, such that no unused space remains, which could otherwise cause problems for the patient. Conventional techniques used for measuring the length of such holes is often done by using a mechanical slide gauge, which is time consuming, and often requires the use of repeated x-ray-control and corrections. See for example, U.S. Pat. No. 8,092,457, and U.S. Patent Publication No. 2008-0255572, the disclosures of which are hereby incorporated herein by reference.

Most orthopedic and/or neurological hand-held drill devices do not provide any means for automatic depth control. Most procedures rely entirely on the surgeons' judgment and skill to estimate the bone cutter depth. This invention provides an automatic depth control for bone drilling.

The precision bone drill of the present invention is an improved and modified version of a device known as the PathFormer device. The PathFormer device is described in U.S. Pat. No. 7,848,799, the disclosure of which is hereby incorporated by reference. See also FDA 510(k) Application No. K052770, approved for the PathFormer device.

The PathFormer device (see FIGS. 1 and 2) is designed and intended for cutting through finger and toe nails, e.g., to release fluid accumulated in the underlying nail bed, for relieving pressure from subungual hematomas (including black toe). The PathFormer device is an electrosurgical hand-held device that cuts holes in fingernails and toenails using mesoscissioning technology. It cuts the nail with a microcutting tool, using tissue impedance as the feedback mechanism for stopping the cutting intervention.

Using the PathFormer device for cutting through finger and toe nails (trephination), one or more microconduits are drilled to specific depths without penetrating the nail bed. The nail plate is cut with a 400 μm diameter tissue cutter in the hand-held device which contains two small electric motors. One motor rotates the cutter, and the second moves the cutter up and down. The motors are powered by a portable 9V power supply. The cutting motor is connected to an electronic control that measures the electrical impedance between the rotating cutter and an electrocardiogram electrode (i.e., counter-electrode) on the patient's skin. This control can be calibrated to reverse the cutting motor at the detection of a pre-set electrical impedance.

Because the nail plate is highly keratinized, it normally has a high electrical impedance, approximately 5 Mohms, as calculated in preliminary experiments. In contrast the normal impedance of the nail bed is much lower, in the 10-20 Kohms range, largely because of the higher saline content of nail bed tissue. During the drilling process, the removal of each successive layer of the nail plate results in a reduction in electrical impedance at the site of the hole. When the measured electrical impedance has decreased to the trigger impedance, the cutting tool instantaneously and automatically pulls away from the nail.

SUMMARY OF THE INVENTION

The precision bone drill of the present invention is an improved and modified version of the original PathFormer device used for drilling microconduits in nails and/or removing stratum corneum. In some embodiments of the bone drill of this invention the bone cutter (e.g., drill bit) serves as one electrode and the nosepiece with an electrically conducting surface that contacts the bone tissue serves as the counter electrode. In some embodiments, the PathFormer device foot switch is replaced with a hand-operated switch.

In certain embodiments, the PathFormer D.C. vertical drive motor is replaced by a stepper motor. When a stepper motor is used, there may be no need for the counterelectrode, as the number of steps controls the depth of the drill bit into the bone. In such cases, long drill bits and drill guides may be employed (e.g., as in arthroscopic surgery) to allow drilling of bone deep inside the body. Depth of drilling is controlled by the number of steps programmed into the drill unit. This allows the user to get as close as possible to the far side of a bone—if that is the desired result, and once the proper depth has been achieved, the drill bit is automatically withdrawn. Depth control in such cases may also be based on changes in the motor current (drag) during the drilling process. As bone is drilled, the motor current will change when marrow is drilled, and then again when bone on the opposite side is being drilled.

In addition, in certain embodiments, the electronic control circuits of the PathFormer drill device have been modified to include one or more of the following features:

(1A) start counting the steps of the vertical drive motor and start drilling once a pre-set trigger impedance is sensed between the bone cutter and the electrically conductive nosepiece, or (1B) start counting the steps of the vertical drive motor and start drilling once a decrease in impedance between the bone cutter and the electrically conductive nosepiece is sensed, or (1C) start counting the steps of the vertical drive motor and start drilling once an increase in cutter motor current is sensed;

(2) stop drilling and reverse the vertical drive motor when the step count reaches a pre-set count (desired hole depth);

(3) include a current load monitor for added depth control, (4) include a forward motion rate or speed adjustment capability, (5) include a reverse rate or speed adjustment capability, and (6) include an end of reverse motion counter that will stop the reverse motion and reset the system for the next forward cycle.

Another embodiment of the invention provides a method for the precision drilling of human or animal bone tissue. The method comprises the following steps;

(a) providing a drill having an electrically conductive bone cutter acting as an electrode and an electrically conducting nosepiece spaced apart from the conductive bone cutter and acting as a counter electrode;

(b) placing the electrically conductive bone cutter and nosepiece into contact with the bone tissue to be drilled;

(c) measuring the electrical impedance between the bone cutter and the nosepiece, or measuring the cutter motor current;

(d) commencing the drilling of the bone tissue and starting the step counter when the impedance between the bone cutter and the nosepiece reaches a pre-set value; or commencing the drilling of the bone tissue and starting the step counter when the impedance between the bone cutter and the nosepiece starts decreasing; or commencing the drilling of the bone tissue and starting the step counter when the cutter motor current starts increasing;

(e) stop drilling and reversing the vertical drive motor voltage when the step counter reaches a pre-set value— as selected by the surgeon based on the drilling requirements of the case; or stop drilling when the vertical drive motor current starts decreasing. Then start drilling a pre-set number (zero or more) of vertical drive motor steps, after which the vertical drive motor is reversed.

It should be appreciated by those persons having ordinary skill in the arts to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

Figure 1:
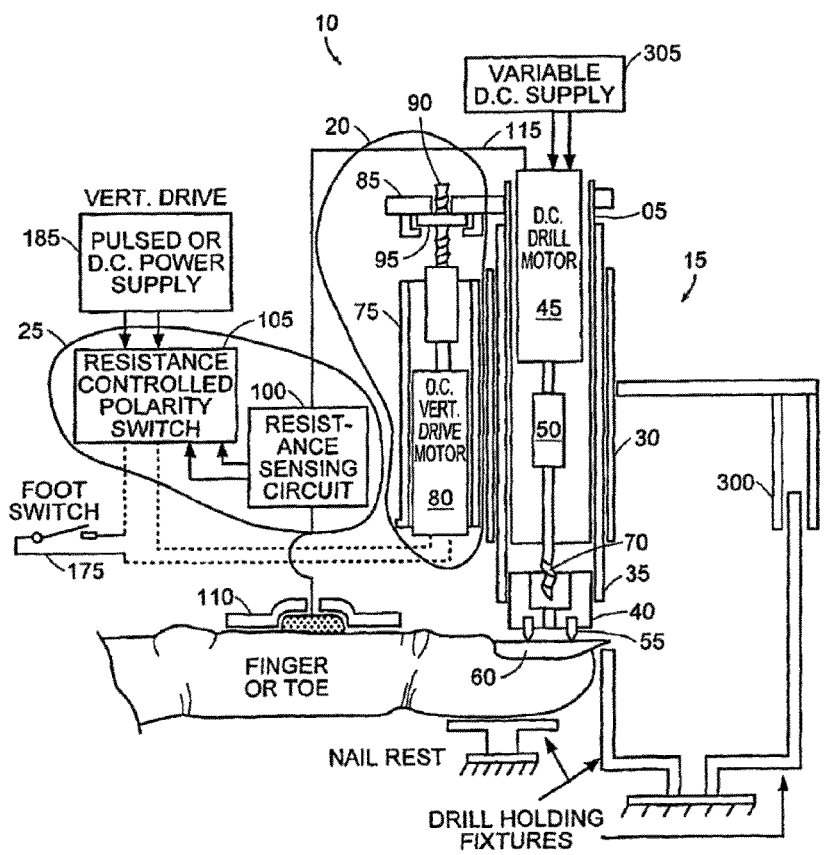
FIG. 1 shows the PathFormer device as described in U.S. Pat. No. 7,848,799. This drawing is labeled as Prior Art.
Figure 2:
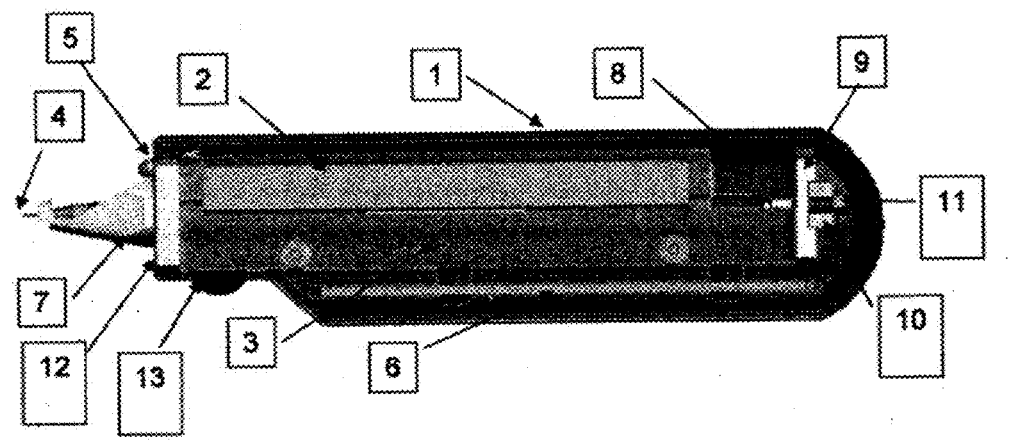
FIG. 2 shows another embodiment of the PathFormer device. This drawing is also labeled as Prior Art. This drawing is taken from the 510(k) Application filed for the PathFormer device.

As described above, the present invention is directed to a drilling device for drilling of human or animal bone tissue, said drilling device comprising:

(a) a housing that includes the drilling components and an electrically conductive nosepiece assembly to be placed in contact with bone tissue to be drilled;

(b) a bone cutter rotated by an electric motor which is mobile in translation in the housing and wherein the bone cutter is electrically conductive and is adapted to be moved into and out of the bone tissue being drilled;

(c) a control module electrically connected to the drilling assembly for controlling the translation of the bone cutter in the housing and into and out of the bone tissue being drilled;

(d) a sensor, electrically connected to the drilling assembly and to the control module for detecting a change in an electrical impedance between the bone cutter and the surface of the bone tissue being drilled when the bone cutter is translated to the bone tissue being drilled; wherein the sensor, upon detection of a change in the electrical impedance corresponding to a transition between air (no load; high electrical impedance) and bone tissue surface, sends a signal to the control module to begin incrementing a step counter;

(e) automatically reverse the direction of the vertical drive motor when the step counter reaches a prespecified count, thereby withdrawing the bone cutter from the bone tissue being drilled, and thereby controlling the depth of the drilled hole. In certain embodiments of the drilling device, the bone cutter is moved toward and away from the bone by a vertical drive motor that may be a stepper motor.

In certain embodiments of the drilling device, the device further comprises a replaceable bone cutter and nosepiece assembly that are attached to the drill device to provide a disposable drilling and sensing drill-stabilizing unit. The bone cutter dimension (length & diameter) is selected by the surgeon based on the needs of the patient.

In certain embodiments of the drilling device, the bone cutter is moved forward and back by a stepping motor which includes a power supply and settable step counter control. In certain embodiments of the drilling device, the step counter control starts counting the steps once a pre-set trigger impedance is sensed between the bone cutter and the electrically conductive impedance sensing electrode or the nosepiece of the housing.

In certain embodiments of the drilling device, the device includes a vertical drive motor step counter that can be pre-set to stop the forward motion of the bone cutter after reaching the desired count, and thus the desired bone cutter depth. In certain embodiments of the drilling device, the device includes a drill load (electrical current) monitor for added depth control of the bone cutter. In certain embodiments of the drilling device, the device includes a forward motion rate or speed adjustment capability, for added depth control of the bone cutter.

In certain embodiments of the drilling device, the device includes a reverse rate or speed adjustment capability. In certain embodiments of the drilling device, the device includes an end of reverse motion counter that will stop the reverse motion and reset the system for the next forward cycle.

In certain embodiments of the drilling device, the device is controlled by the control module such that after the initial identification of the bone surface, the bone cutter, with a foot having no anchor pins, rapidly travels a preselected small number of steps into the bone and the same number of steps back. The process is repeated at several sites on the bone by laterally moving the device on the bone to create a pattern or to locally smooth or flatten the surface of the bone.

In certain embodiments of the drilling device, the device includes means for controlling the desired depth of the drilling. One such means is provided by using an interface that records the dimensions of the orthopedic component that will be inserted into the drilled hole, and the control module of the device records these data to provide the control of the drilling depth.

In one example of this depth control means, the orthopedic hardware manufacturer can include a bar code on each package of the hardware giving data for the length of the hole needed for the orthopedic hardware to be installed. The package would then be scanned by means of a commercial bar code reader connected to the drilling device (e.g., permanently, temporarily or wirelessly), such that the data are provided to the control module, thereby permitting the hole depth to be automatically programmed into the on-board control module.

The drilling device could also contain a readout that would give the surgeon the code for length and diameter of the bone cutter to be installed in the device for a particular type of hardware.

Another embodiment of the invention is directed to a device for drilling of human or animal bone tissue, said drilling device comprising:

(a) a housing that includes a drilling assembly and an electrically conductive nosepiece assembly to be placed in contact with bone tissue to be drilled;

(b) a bone cutter rotated by an electric motor which is mobile in translation in the housing and wherein the bone cutter is electrically conductive and is adapted to be moved into and out of the bone tissue being drilled;

(c) a control module electrically connected to the drilling assembly for controlling the translation of the bone cutter in the housing and into and out of the bone tissue being drilled;

(d) a sensor, electrically connected to the drilling assembly and to the control module for detecting a change in electrical current through the cutter motor; wherein the sensor, upon detection of a change in the electrical current through the cutter motor corresponding to a transition between air (no load) and bone tissue surface, sends a signal to the control module to begin incrementing a step counter;

(e) automatically reverse the direction of the bone cutter when the step counter reaches a prespecified count, thereby withdrawing the bone cutter from the bone tissue being drilled, and thereby controlling the depth of the drilling.

(f) automatically reverse the direction of the vertical drive motor when the vertical drive motor current starts decreasing thereby withdrawing the cutter, as described above.

Another embodiment of the invention is a method for conducting drilling of human or animal bone comprising the following steps:

(a) providing an embodiment of the precision bone drill device of this invention, the device having an electrically conductive bone cutter and an electrically conducting nosepiece assembly spaced from the conductive bone cutter, and acting as a counter electrode;

(b) placing the conductive bone cutter and nosepiece assembly into contact with the bone tissue to be drilled;

(c) commencing the drilling of the bone tissue to be drilled;

(d) measuring an electrical impedance between the bone cutter tip and the counter electrode to obtain impedance data of the bone tissue being drilled;

(e) analyzing the electrical impedance data by a control module and starting the increment of a step counter when the electrical impedance decreases; and (f) controlling the depth of drilling in the bone tissue by incrementing the step counter with every step of the motor until a prespecified count is reached.

Another embodiment of the invention is a method for drilling of human or animal bone comprising the following steps:

(a) providing an embodiment of the precision bone drill of this invention, the device having an electrically conductive bone cutter and an electrically conducting nosepiece assembly spaced apart from the conductive bone cutter, and acting as a counter electrode;

(b) placing the nosepiece assembly into contact with the bone tissue to be drilled;

(c) measuring the electrical impedance between the nosepiece and the conductive cutter;

(d) thereafter commencing the drilling of the bone tissue to be drilled;

(e) measuring the electrical current through the cutter motor;

(f) analyzing the electrical current data by a control module and starting the increment of a step counter when the cutter motor current increases; and (g) controlling the depth of drilling in the bone tissue by incrementing the step counter with every step of the motor until a prespecified count is reached.

Figure 5:
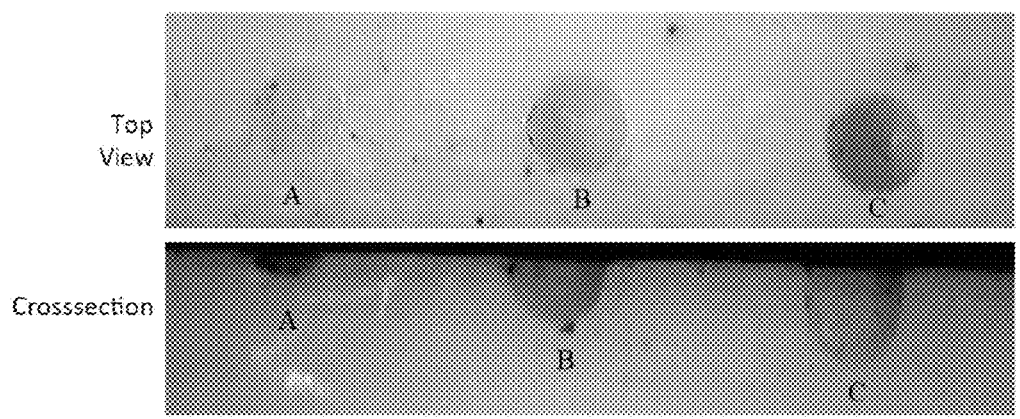
FIG. 5 shows an example of bone drilling depth precision. Three holes were drilled into bovine bone by an embodiment of the Precision Bone Drill using a 0.030" diameter ballnose bone cutter. The holes, spaced 0.075" apart, are 0.010", 0.020", and 0.030" deep, from left to right, respectively.

As illustrated in FIG. 5, the precision drill of this invention reliably drills holes in bones to precise depths, i.e., to a depth that is preselected by the surgeon. Diameter of the holes is determined by the particular bone cutter, selected by the surgeon based on the needs of the patient.

Figure 3:
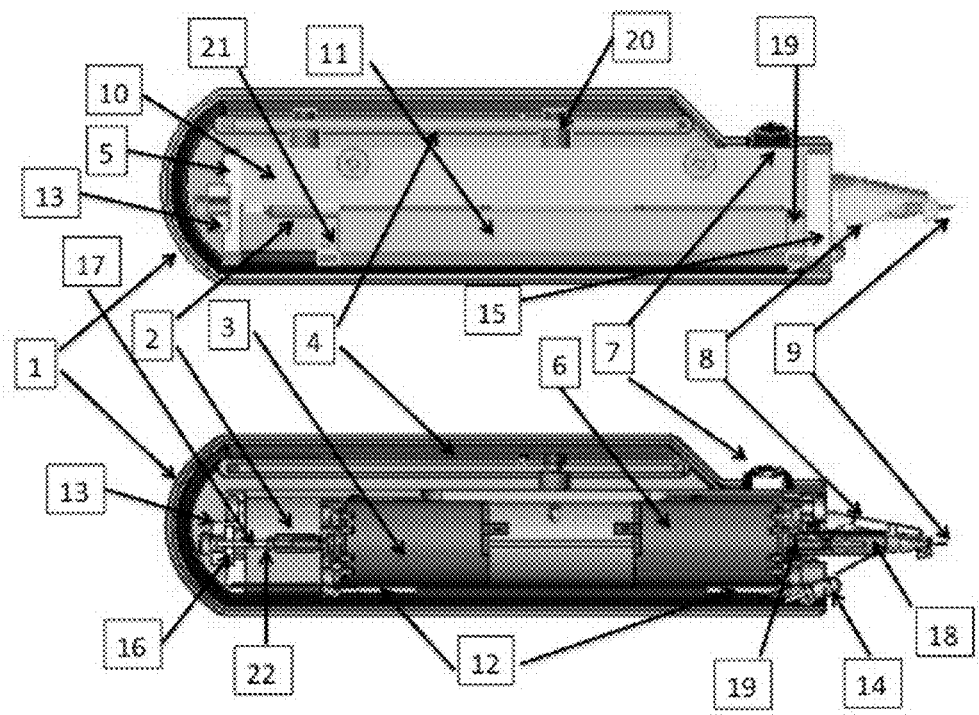
FIG. 3 shows an embodiment of the Precision Bone Drill of the present invention.
Figure 4:
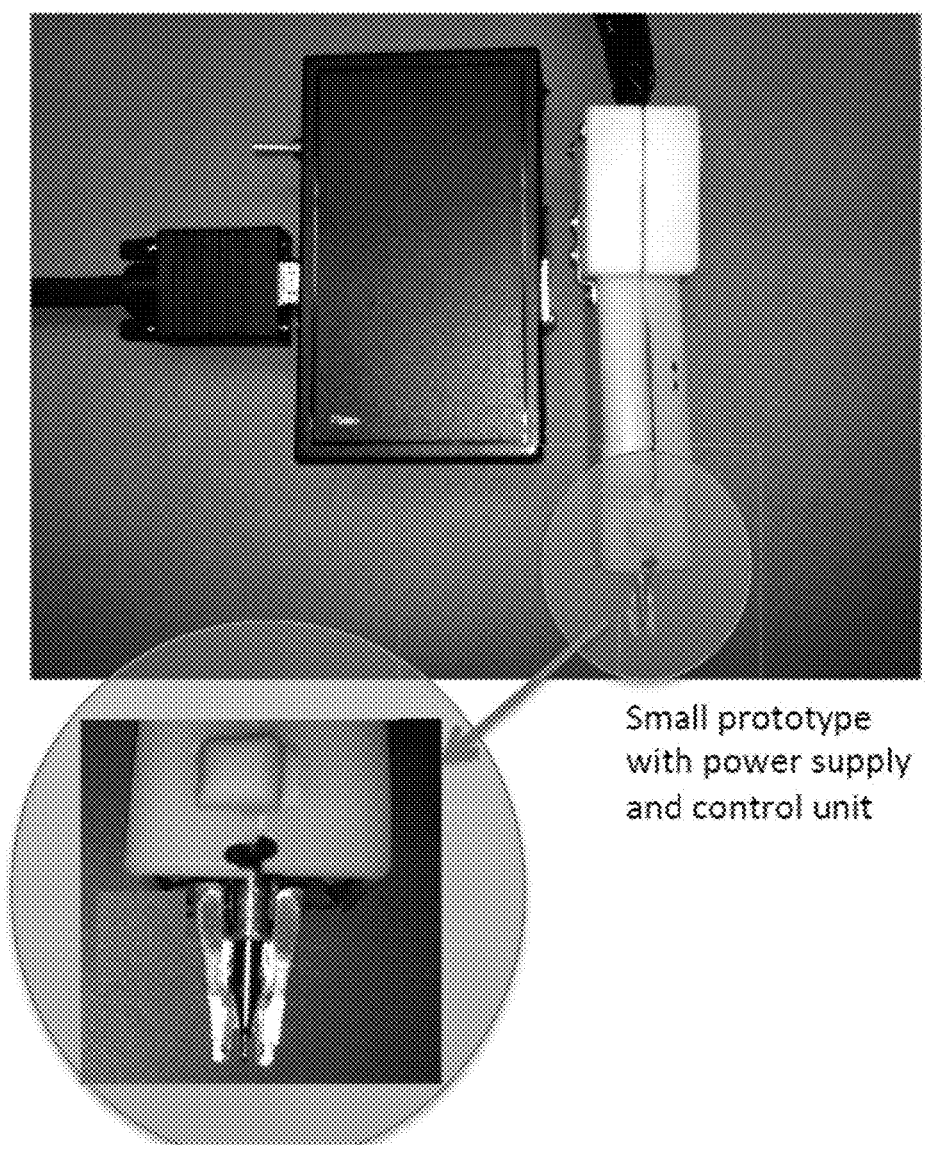
FIG. 4 shows an embodiment of the Precision Bone Drill of the present invention, with a detailed view of the bone cutter and nosepiece parts of the device.

As illustrated in FIGS. 3 and 4, the device has a nosepiece that is placed against the bone to orient the bone cutter relative to the curved surface of the bone. Anchor pins in the nosepiece stabilize the device and eliminate lateral motion while drilling. If these anchor pins are not provided, then the drill can be used to allow surface modifications of the bone. The precision drill of this invention uses two disposables: (1) the bone cutter and (2) the nosepiece. The bone cutter and the nosepiece can be made out of any suitable electrically conducting materials such as any number of known metals and metal alloys.

The nosepiece also serves as the counter-electrode for electrical impedance sensing. The impedance between the bone cutter and the nosepiece on the bone surface is continually measured to signal the instant that the bone cutter touches the bone and the high electrical impedance between them drops by orders of magnitude during the drilling process. This change in electrical impedance starts the count of the stepper motor that moves the bone cutter into the bone. Once the pre-programmed depth is reached, the bone cutter is automatically retracted out and away from the bone rapidly.

To use the precision drill of this invention the surgeon presses the device against the bone to push the anchor pins (approximately 0.003" long) slightly into the bone surface (preventing the drill from moving laterally). The surgeon can tilt the drill to the desired angle on the bone surface and drill a hole of pre-set depth by pressing the actuator switch until the bone cutter drills the hole and retracts out of the bone. Releasing the switch while drilling will cause the bone cutter to immediately retract, acting as a fail-safe feature.

The device is equipped with a programmable control module that detects when the drilling device touches the surface of the bone by sensing the change in electrical impedance between the bone cutter and the device nosepiece that rests against the bone surface. This nosepiece contains small, sharp pins that penetrate the bone slightly and prevent lateral motion (sliding) on the bone by the device. The electrical impedance is very high between the bone cutter and nosepiece until the cutter touches the bone surface, when the electrical impedance drops orders of magnitude due to the high electrical conductivity of the body's natural saline environment present on the patient's bone.

Precise Depth Function

The depth of the hole being drilled can be programmed into the control module as a certain number of steps to be taken by a 'stepper' motor that turns a lead screw. The stepper motor is mounted to the moving carriage of the device to which the cutter motor of the device is attached. The stepper motor turns a lead screw that is threaded through a nut attached to the stationary frame of the device. This moves the moving carriage along guide pins in the stationary frame to which the nosepiece of the device is attached. Thus, the stepper motor turns the lead screw to move the bone cutter and cutter motor toward and away from the bone to be drilled. In certain embodiments, the stepper motor can be mounted on the stationary frame and the nut can be attached to the moving carriage.

The control module can be programmed to send a precise number of electrical pulses to the stepper motor. Each pulse moves the stepper motor one step, the step counter counts the stepper motor pulses. The surgeon places the cutter tip against the bone, presses and holds the actuator switch (or optional foot switch) and the spinning bone cutter is moved the distance programmed into the control module to drill the hole to the predetermined depth. Having moved that predetermined distance, the cutter is automatically withdrawn from the hole. The surgeon has the option of releasing the actuator switch and the bone cutter is automatically rapidly withdrawn from the hole as a 'fail-safe' feature. The depth is accurate to within plus or minus 0.1 mm of the depth setting or better.

In certain embodiments, the bone cutter and cutter motor (electric or air powered) are mounted on a moveable carriage, and positioned by a stepper motor-driven lead screw.

Figure 6:
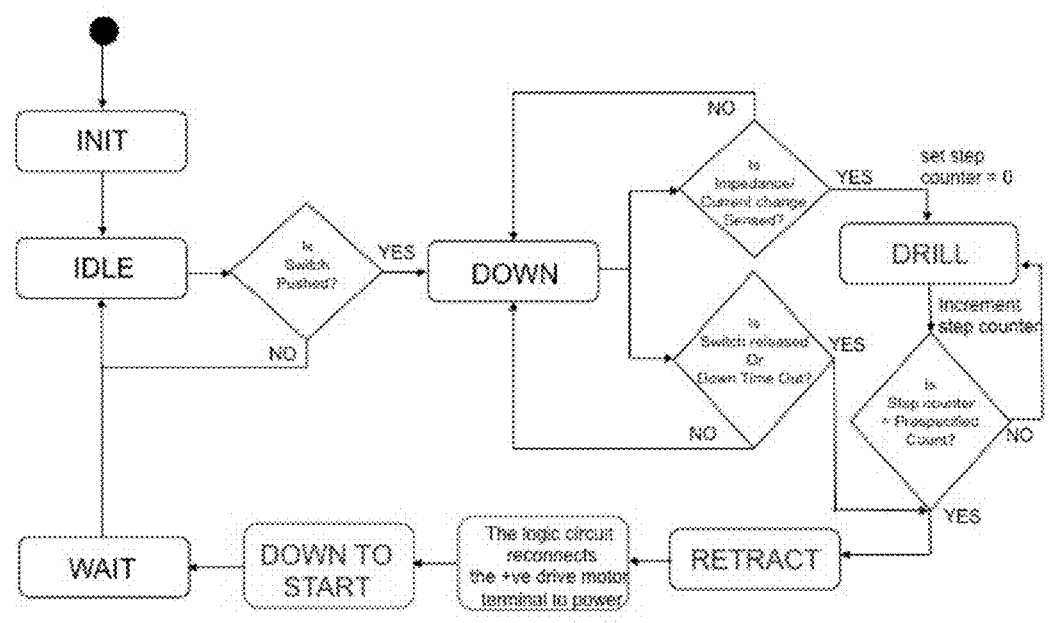
FIG. 6 shows a flow chart of the control programming for an embodiment of the Precision Bone Drill of the present invention.

In certain embodiments, an on-board control module, programmed as per FIG. 6, measures the electrical impedance and acting in conjunction with the stepper motor, controls the position of the bone cutter, its approach speed, its precise position while drilling and its withdrawal rate.

In certain embodiments, the cutter motor in the bone drill device runs at a fixed voltage. A control module turns the cutter motor on and off. This control module also controls the carriage motor that moves the bone cutter motor toward or away from the bone. In the drilling cycle, the cutter runs at no load and low motor current while moving toward the bone. When it begins drilling the bone, the load on the bone cutter increases the motor current. This increase is sensed by the control module. Once the cutter nears the cortical side of the bone, the remaining, thin, undrilled bone becomes more flexible reducing the load, and the cutter motor current drops. The control module senses this drop in current, and signals the carriage motor to rapidly retract the bone cutter from the bone, thus stopping a few thousandths of an inch short of drilling completely through the bone. This prevents damaging the underlying tissue, blood vessels and nerves on the cortical side of the bone.

Through Bone Function

In this mode, which can be employed in all of the embodiments described herein, the control module monitors the cutter motor electrical current. The surgeon actuates the stepper motor that moves the bone cutter toward the bone. Drilling commences and the motor current increases due to the increased torque on the cutter motor from the drilling process. The bone cutter will move through the bone and through the marrow, and as it reaches the far cortex of the bone, the drill current will diminish as the amount of remaining bone thins reducing the load, and will diminish further as the bone cutter emerges from the bone. At this point the control module will stop the forward motion of the bone cutter and initiate the stepping motor count. This stepping motor count has been pre-set by the surgeon and allows the bone cutter to move out of the bone and into the soft tissues beyond the far cortex. The amount of this over-travel into the tissues is determined by the stepping motor count as set by the surgeon prior to drilling. Thus, the bone cutter protrusion beyond the far cortex can be controlled to within approximately 0.2 mm of the over travel setting.

In this thru-bone function, the bone cutter can encounter low load (torque) conditions on larger bones in their center comprising marrow and/or softer cancellous bone. The surgeon can override the low torque/motor current conditions going through such regions and return the drill to its 'hard bone, high current' mode once through the marrow region by pressing the actuator switch or optional foot switch more firmly to initiate the stepper motor count interruption until the bone cutter encounters hard bone beyond the cancellous region. As the motor current rises upon entering the 'hard bone, high current' condition, the onboard control module will cause the stepper count to resume from its point of interruption.

EXAMPLE

A cross-section of the bone drill and its components are shown in FIG. 3. The different parts are numbered in the caption. The bone drill consists of the following main functional elements: a bone cutter, foot, a bone cutter drive motor and a vertical drive motor. The cutter drive motor, mounted on a movable chassis, rotates the bone cutter. The vertical drive motor coupled to a lead screw steps the movable chassis toward/into or away/out of the bone tissue.

The components of the bone drill are housed in a plastic outer housing (Parts 1 and 2 in FIG. 3) that is split into fully conforming halves. The hand-actuated switch to operate the drill protrudes through an opening in the housing. The cables to the sensing electrodes are connected to the circuit board. The cables to the power supply are connected through an access port toward the back of the housing (FIG. 4).

The bone drill chassis has two parts: a stationary frame (Part 10 in FIG. 3) and a movable carriage (part 11 in FIG. 3). The two parts are connected to each other through a top plate (Part 5 in FIG. 3) and a bottom plate (Part 15 in FIG. 3) by pairs of guide pins (Part 12) in each plate. The cutter motor is connected to the end of the movable carriage by screws to its end plate (Part 19). The vertical drive motor is connected to the movable carriage by screws to its end plate (Part 21).

The cutter and vertical motor end plates have pairs of holes in them, the moveable carriage has sufficiently long, oversized holes that match the end plate holes. The holes in the plate (part 5) and bottom plate (plate 15) have guide pins pressed into them. These guide pins pass through the clearance holes in the cutter motor end plate (Part 19) and the vertical drive end plate (Part 21) and further through the holes in the movable carriage. Thus the assembled movable carriage can slide on the guide pins in the stationary frame. The lead screw (Part 17) that passes through a nut keeper (Part 13) holds the lead screw nut (Part 16). The lead screw is connected to the vertical motor by a coupling element (Part 2).

The control module electronics, that control the two motors, are contained in two circuit boards. One circuit board (Part 4) that is fixed to the stationary frame contains an onboard control module. The circuitry on this board measures the impedance between the bone cutter and the nosepiece. It also sends the motion direction and on/off signals to the two motors (Part 6 and Part 3). The second circuit board is located inside the external power supply unit (FIG. 4). This board has a stepper motor controller (PRECIstep, Faulhaber) that controls the vertical drive motor. In addition, the power supply unit has a variable voltage regulator that powers the cutter motor and the first circuit board. Conductors from the circuit board and power supply unit connect to the motors, cutter and the nosepiece.

The drill device with its associated electronics is run by a rechargeable battery housed in the power supply unit. A white 3 mm LED (RL3-W6045, commercially available at superbridgeleds.com) may be used to illuminate the drilling area. The LED (light emitting diode, Part 14 in FIG. 3) is powered by the control circuit. The cutter is held in place by a chuck, with three equally spaced slits, which is attached to the spindle of the cutter motor. The nosepiece (Part 9 in FIG. 3), made of or coated with an electrically conducting material, is fixed to the device with a lock-in screw. This part encloses, but does not physically contact the cutter. In the surface of the nosepiece that contacts the bone surface, two sharp, protruding anchor pins, approximately 0.003" long, are embedded into the bone.

The motor that drives the cutter is a 6V DC motor (1524T006S, Faulhaber). It is operated at 10,000 rpm using a 6 V pulsed input (50% duty cycle). The vertical drive motor is a two-phase 6V stepper motor (ADM0620-2R-ww-ee; Faulhaber) that is attached to the lead screw and the movable chassis. The lead screw moves in a nut fixed to the stationary frame thus moving the cutter towards or away from the cutting surface.

The onboard control module regulates the direction and the pulsing signals of the stepper motor controller. The onboard control module also keeps count of the number of steps taken by the vertical drive motor. The impedance between the cutter and the nosepiece is measured with a 2 kHz, 0.1 V square wave input. The impedance is compared with a pre-set trigger impedance. The difference signal is amplified by a two-stage amplifier, the output of which is used to start/stop the cutter motor and start/stop/reverse the vertical drive motor.

The bone drill is assembled, from the parts listed in FIG. 3, as described below. Insert a pair of longer guide pins (Part 12) through the top plate (Part 5) with the tapered ends into the holes and gently press each in. Place the lead nut (Part 16) in the groove of the top plate (Part 5) and place the nut keeper (Part 13) on top in the groove and put in the two longer screws. Crimp the screws' bottom to avoid the screws loosening. Apply some epoxy on the motor shaft and push the motor coupling (Part 2) on the motor shaft. Let it cure. Fix the vertical drive motor plate (Part 21) on to the vertical drive (stepper) motor (Part 3) and fix the cutter motor plate (Part 19) to the cutter motor (Part 6) using small screws. Insert the lead screw (Part 17) through the top plate (Part 5). Insert the lock nut (Part 22) half way into the lead screw (Part 17).

Connect the vertical drive motor plate (Part 21) to the vertical drive (stepper) motor with screws. Add some glue into the motor coupling on the lead screw side. Immediately screw the lead screw as far as possible into the motor coupling. Bring down the lock nut to be flush with the motor coupling. Add more glue around the nut. Tighten firmly against the motor coupling. Let it cure. Put some glue on the cutter motor shaft and insert the shaft (Part 18) into the cutter chuck and let it cure.

Insert shorter guide pins into the bottom plate and press each it in to be flush with the plate surface. Scratch the surface of the cutter motor close to the terminal end with a knife and expose a 1 mm$^2$ area of the surface. Apply a tiny amount of solder on the exposed area, and solder the impedance-sensing lead from the circuit board to the motor body. Cover the cutter motor body with an electrical tape.

Attach the cutter motor plate of the cutter motor to the other end of the moving carriage. Insert the guide pins of the bottom plate into the moving carriage. Connect wires to the two motor leads. Run the wires through the opening in the stationary frame. Solder the wires to the printed circuit board (PCB, Part 4). Ensure proper polarity of the motor. Screw the stationary frame to the top plate and the bottom plate (four screws). Connect the PCB to the stationary frame with two long screws and spacers (Part 20). Clip the two leads of the white LED (Part 14) and solder two wires and connect the wires to power and ground through a series resistor (220 ohms). Attach two leads from the switch on the circuit board to the actuator switch (Part 7). Tape the switch on to the stationary frame with adhesive. Place the rubber cover over the actuator switch (Part 7). Attach the power cable to power connector on the PCB. Place the two halves of the housing (Part 1) around the moving carriage and stationary frame and attach them using the flat screws.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of drilling through bone comprising the steps of:
   (i) providing a drilling device having an electrically conductive bone cutter and an electrically conducting nosepiece assembly spaced from the conductive bone cutter, and acting as a counter electrode;
(ii) placing the conductive bone cutter and nosepiece assembly into contact with the bone tissue to be drilled; and
(iii) commencing the drilling of the bone tissue; said drilling device further comprising:
(a) a housing that includes a drilling assembly and an electrically conductive nosepiece assembly to be placed in contact with bone tissue to be drilled;
(b) a bone cutter rotated by an electric motor which is mobile in translation in the housing and wherein the bone cutter is electrically conductive and is adapted to be moved into and out of the bone tissue being drilled;
(c) a printed circuit board control module electrically connected to the drilling assembly for controlling the translation of the bone cutter in the housing and into and out of the bone tissue being drilled;
(d) a sensor, electrically connected to the drilling assembly and to the control module, for detecting a change in an electrical impedance between the bone cutter and the surface of the bone tissue being drilled; wherein upon detection, by the sensor, of a change in the electrical impedance corresponding to a transition between air (no load; high electrical impedance) and bone tissue surface, sends a signal to the control module begins incrementing a step counter; and
(e) wherein the direction of the vertical drive motor is automatically reversed when the step counter reaches a prespecified count, thereby withdrawing the bone cutter from the bone tissue being drilled, and thereby controlling the depth of the drilled hole.

2. The method of claim 1, wherein the bone cutter is moved toward and away from the bone by a vertical drive motor that comprises a stepper motor.

3. The method of claim 2, wherein the stepper motor further includes a stepping power supply and settable counter control.

4. The method of claim 3, wherein the counter control starts counting the steps once a pre-set trigger impedance is sensed between the bone cutter and the electrically conductive impedance sensing electrode or the nosepiece of the housing.

5. The method of claim 4, wherein the drilling device further includes a vertical drive motor step counter pre-set to stop the forward motion of the bone cutter after reaching the desired count, and thus the desired bone cutter depth.

6. The method of claim 1, wherein the drilling device further comprises a replaceable bone cutter and nosepiece assembly that are attached to the drill device to provide a disposable drilling and sensing drill-stabilizing unit.

7. The method of claim 1, wherein the drilling device further comprises a drill electrical current load monitor for depth control of the bone cutter.

8. The method of claim 1, wherein the drilling device further comprises a forward motion rate or speed adjustment capability, for added depth control of the bone cutter.

9. The method of claim 1, wherein the drilling device further comprises including a reverse rate or speed adjustment capability.

10. The method of claim 1, wherein the drilling device further comprises an end of reverse motion counter to stop the reverse motion and reset the system for the next forward cycle.

11. A method for conducting drilling of human or animal bone comprising the following steps:
providing a drill device having an electrically conductive bone cutter and an electrically conducting nosepiece assembly spaced from the conductive bone cutter, and acting as a counter electrode;
placing the electrically conductive bone cutter and nosepiece assembly into contact with the bone tissue to be drilled;
commencing the drilling of the bone tissue to be drilled;
measuring an electrical impedance between the bone cutter tip and the counter electrode to obtain impedance data of the bone tissue being drilled;
analyzing the electrical impedance data by a printed circuit board control module and starting the increment of a step counter when the electrical impedance decreases; and
controlling the depth of drilling in the bone tissue by incrementing the step counter with every step of the motor until a prespecified count is reached.

12. A drilling device for drilling of human or animal bone tissue, said drilling device comprising:
(a) a housing that includes a drilling assembly and an electrically conductive nosepiece assembly to be placed in contact with bone tissue to be drilled;
(b) a bone cutter rotated by an electric motor which is mobile in translation in the housing and wherein the bone cutter is electrically conductive and is adapted to be moved into and out of the bone tissue being drilled;
(c) a printed circuit board control module electrically connected to the drilling assembly for controlling the translation of the bone cutter in the housing and into and out of the bone tissue being drilled;
(d) a sensor, electrically connected to the drilling assembly and to the control module, for detecting a change in the electrical current through the cutter motor;
wherein, upon detection, by the sensor, of a change in the electrical current through the cutter motor corresponding to a transition between air (no load) and bone tissue surface, the control module begins incrementing a step counter; and
(e) wherein the direction of the vertical drive motor is reversed when the step counter reaches a prespecified count, thereby withdrawing the bone cutter from the bone tissue being drilled, and thereby controlling the depth of the drilling.

13. The drilling device of claim 12, wherein the desired depth is set using an interface device that records the dimensions of the orthopedic component that will be inserted into the drilled hole.

14. The drilling device of claim 12, wherein after the initial identification of the bone surface, the bone cutter rapidly travels a preselected number of steps into the bone and the same number of steps back.

15. The drilling device of claim 14, wherein the nosepiece or foot does not include any anchor pins, thereby allowing the bone cutter to be moved during drilling.

16. The drilling device of claim 12, wherein the nosepiece or foot further includes anchor pins to prevent wander of the bone cutter during drilling.

17. The drilling device of claim 12, wherein the sensor comprises an electrode in contact with the skin of the human or animal on which drilling of bone is to be conducted.

18. A drilling device for drilling of human or animal bone tissue, said drilling device comprising:
(a) a housing that includes a drilling assembly and an electrically conductive nosepiece assembly to be placed in contact with bone tissue to be drilled;
(b) a bone cutter rotated by an electric motor which is mobile in translation in the housing and wherein the bone cutter is electrically conductive and is adapted to be moved into and out of the bone tissue being drilled;

(c) a printed circuit board control module electrically connected to the drilling assembly for controlling the translation of the bone cutter in the housing and into and out of the bone tissue being drilled;

(d) a sensor, electrically connected to the drilling assembly and to the control module, for detecting a change in an electrical impedance between the bone cutter and the surface of the bone tissue being drilled when the bone cutter is translated in the bone tissue being drilled; wherein upon detection, by the sensor, of a change in the electrical impedance corresponding to a transition between no load and high electrical impedance, and bone tissue surface, sends a signal to the control module begins incrementing a step counter; and (e) wherein the direction of the vertical drive motor is reversed when the step counter reaches a prespecified count, thereby withdrawing the bone cutter from the bone tissue being drilled, and thereby controlling the depth of the drilled hole.

19. The drilling device of claim 18, wherein the sensor comprises an electrode in contact with the skin of the human or animal on which drilling of bone is to be conducted.

20. The drilling device of claim 18, wherein the sensor comprises a conductive sleeve mounted around the cutter.

21. The device of claim 18, wherein multiple changes in the material being drilled are detected, such impedance or current changes including when the drill contacts the bone surface, enters the marrow, leaves the marrow and enters the bone again, and finally when it reaches the cortical end of the bone; and wherein, depending on the surgeon's requirement, the device is programmed to retract at the first, second, third, or fourth change in impedance or current.

* * * * *